(12) United States Patent
Jaeb et al.

(10) Patent No.: US 8,273,074 B2
(45) Date of Patent: Sep. 25, 2012

(54) WOUND EXUDATE REMOVAL AND ISOLATION SYSTEM

(75) Inventors: Jonathan Jaeb, Boerne, TX (US); Tab Randolph, San Antonio, TX (US); Randall Kelch, San Antonio, TX (US); Xiaolu Zheng, San Antonio, TX (US); Devin Ginther, Converse, TX (US); Tianning Xu, San Antonio, TX (US); Jennifer N. Novak, Houston, TX (US); T. Blane Sanders, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 800 days.

(21) Appl. No.: 11/634,719

(22) Filed: Dec. 6, 2006

(65) Prior Publication Data

US 2007/0260226 A1 Nov. 8, 2007

Related U.S. Application Data

(60) Provisional application No. 60/742,755, filed on Dec. 6, 2005.

(51) Int. Cl.
*A61M 27/00* (2006.01)
(52) U.S. Cl. ............ 604/543; 604/19; 604/317
(58) Field of Classification Search ............ 604/19, 604/27, 32, 38, 99.04, 224, 389, 313, 540–543, 604/317–320; 602/2
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Foower, Jr. |

(Continued)

FOREIGN PATENT DOCUMENTS

AU 550575 A1 8/1982

(Continued)

OTHER PUBLICATIONS

International Search Report and Written Opinion dated Aug. 20, 2008; PCT International Application No. PCT/US08/73749.

(Continued)

*Primary Examiner* — Tatyana Zalukaeva
*Assistant Examiner* — Benedict L Hanrahan

(57) ABSTRACT

A wound exudate removal and isolation system includes a porous dressing, a canister in fluid communication with the dressing, and a first valve positioned between the dressing and the canister. The first valve is positionable between an open position and a closed position. A disposal line is fluidly connected to the canister and includes a second valve that is positionable between an open position and a closed position. A pump is fluidly connected to the canister and is configured to draw wound exudate from the dressing into the canister when the first valve is open and the second valve is closed. The pump is configured to force wound exudate from the canister into the disposal line when the first valve is closed and the second valve is open.

20 Claims, 3 Drawing Sheets

U.S. PATENT DOCUMENTS

| | | | |
|---|---|---|---|
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,978,855 A | 9/1976 | McRae et al. | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,834,110 A * | 5/1989 | Richard | 600/573 |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,071,409 A | 12/1991 | Rosenberg | |
| 5,086,170 A | 2/1992 | Luheshi et al. | |
| 5,092,858 A | 3/1992 | Benson et al. | |
| 5,100,395 A | 3/1992 | Rosenberg | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta | |
| 5,645,081 A | 7/1997 | Argenta et al. | |
| 5,670,050 A | 9/1997 | Brose et al. | |
| 6,071,267 A | 6/2000 | Zamierowski | |
| 6,135,116 A | 10/2000 | Vogel et al. | |
| 6,231,532 B1 | 5/2001 | Watson et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,641,592 B1 | 11/2003 | Sauer | |
| 6,814,079 B2 | 11/2004 | Heaton et al. | |
| 7,004,915 B2 * | 2/2006 | Boynton et al. | 601/6 |
| 7,198,046 B1 * | 4/2007 | Argenta et al. | 128/897 |
| 2001/0029956 A1 | 10/2001 | Argenta et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0161317 A1 * | 10/2002 | Risk et al. | 602/2 |
| 2002/0172709 A1 * | 11/2002 | Nielsen et al. | 424/445 |
| 2004/0006319 A1 | 1/2004 | Lina et al. | |
| 2004/0064132 A1 | 4/2004 | Boehringer et al. | |
| 2004/0225252 A1 | 11/2004 | Gillespie et al. | |
| 2005/0090787 A1 | 4/2005 | Risk et al. | |
| 2006/0155260 A1 * | 7/2006 | Blott et al. | 604/543 |
| 2009/0306609 A1 * | 12/2009 | Blott et al. | 604/305 |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2005/046761 A1 | 5/2005 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gork , U.S.S.R. 1987 ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Australian Examination Report date mailed Jun. 5, 2009; Australian Patent Application No. 2006321892.

Michael S. Miller et al., "Negative pressure wound therapy options promote patient care," BioMechanics Archives: Sep. 2006.

International Search Report and Written Opinion dated Aug. 28, 2008; PCT International Application No. PCT/US06/46667.

\* cited by examiner

WOUND EXUDATE REMOVAL AND ISOLATION SYSTEM

CROSS REFERENCE TO RELATED APPLICATIONS

This application claims the benefit of U.S. Provisional Application No. 60/742,755, filed Dec. 6, 2005, which is hereby incorporated by reference.

BACKGROUND OF THE INVENTION

1. Field of the Invention

The present invention pertains to wound management. More particularly, the present invention pertains to a wound management system that employs reduced pressure to remove wound exudate and a dressing that will contain and isolate the wound where the dressing must remain on the wound for a prolonged period of time.

2. Description of Related Art

The recent protracted combat operations of the U.S. Armed Forces in both Afghanistan and Iraq have been remarkable in the comparatively low level of fatalities compared to other conflict involving U.S. Armed Forces, such as the combat operations in Viet Nam. The reason for the comparatively low level of fatalities is because of the dramatic improvements that have been made in protective body armor and medical care. Significant improvements have been made to procedures and techniques for stabilizing and removing injured personnel from the battlefield to a facility where medical care may be administered by personnel with proper equipment. While there has been a dramatic decrease in the loss of life, there also has been a corresponding increase in the number of service members wounded. As in many combat situations, a frequent injury to those in ground combat operations is a deep, traumatic wound. Many military trauma wounds are inherently contaminated and can become severely infected because of prolonged contact with the ground on the battlefield or lengthy periods without treatment. Field medics are taught how to irrigate and/or clean deep wounds and then cover the wound with some type of wound dressing. The wound dressing performs several functions. A dressing often includes a powder, an ointment, or a salve, which may kill some of the toxic bacteria that have entered the wound. Second, the dressing covers the wound to help prevent entry of additional toxic bacteria. Third, the dressing decreases the chance of cross-contaminating other wounds on a patient's body. Fourth, the dressing absorbs fluids or exudate from the wound.

When wounds are large or deep, however, several treatment problems arise. Because medical evacuation routes can extend thousands of miles, it is not uncommon for wounded soldiers to experience several days in the medical evacuation process. While wounded personnel are in transport, it is generally not possible to provide the type of wound treatment care available in a hospital. A gauze dressing may not have sufficient fluid retention capacity to adequately absorb all of the exudate from some wounds, and so may become saturated with exudate. Saturated dressings may not be easily exchanged for non-saturated dressings during medical evacuation and transport by aircraft or ground/water transport vehicles. A typical mounting arrangement in medical transport/evacuation vehicles involves stacking patient gurneys three or four high, often against a wall or bulkhead. Such stacking of gurneys may limit access to exudating wounds of those patients on the gurneys such that medical personnel often cannot readily tend to dressings or any other equipment used to protect wounds.

During all parts of the medical evacuation process, there is a need to provide wound exudate management and wound isolation with the wound contained in a closed protective environment. Further, there is a need to remove and isolate wound exudate so that the wound exudate, a biohazardous material, can be collected and properly discarded. Such removal and isolation of wound exudate will reduce cross-contamination, reduce the risk of infection, and facilitate effective wound management during the transport of injured soldiers. There is a need to provide a system that is compact so that it may be easily carried and is not dependent on any external source of energy for operation. Finally, there is a need to provide a system that will be U.S. Military Flight Certified, a non-capital level asset, and disposable.

BRIEF SUMMARY OF THE INVENTION

The problems presented by existing wound isolation systems and methods are solved by the systems and methods of the present invention. A wound exudate removal and isolation system in accordance with one embodiment of the present invention includes a porous dressing, a canister in fluid communication with the porous dressing, and a first valve positioned between the porous dressing and the canister. The first valve is positionable in an open position to allow fluid flow and a closed position to prevent fluid flow between the porous dressing and the canister. A disposal line is fluidly connected to the canister, and a second valve is operably positioned within the disposal line. The second valve is positionable in an open position to allow fluid flow and a closed position to prevent fluid flow through the disposal line. A pump is positioned in fluid communication with the canister and is operable to draw wound exudate from the porous dressing into the canister when the first valve is open and the second valve is closed. The pump further is operable to force wound exudate from the canister into the disposal line when the first valve is closed and the second valve is open.

In accordance with another embodiment of the present invention, a wound treatment apparatus includes a means for dressing a wound, a means for drawing exudate from the wound into a canister, a means for isolating the wound, and a means for forcing exudate from the canister.

In accordance with another embodiment of the present invention, a wound stasis and isolation apparatus includes an open-cell, reticulated foam dressing having an average pore size less than about 200 microns. A drape is provided to cover the foam dressing and the wound. A pump is positioned in fluid communication with the foam dressing to draw wound exudate from the wound at a pressure less than about 125 mmHg to maintain wound drainage and moisture control at the wound but minimize tissue in-growth into the foam dressing.

In accordance with another embodiment of the present invention, a method of providing stasis and isolation to a wound is provided. The method includes positioning an open-cell, reticulated foam dressing adjacent the wound, the foam dressing having an average pore size less than about 200 microns. A drape is positioned over the foam dressing and the wound, and a reduced pressure of less than about 100 mmHg is applied to the foam dressing.

Other objects, features, and advantages of the present invention will become apparent with reference to the drawings and detailed description that follow.

DETAILED DESCRIPTION OF A PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
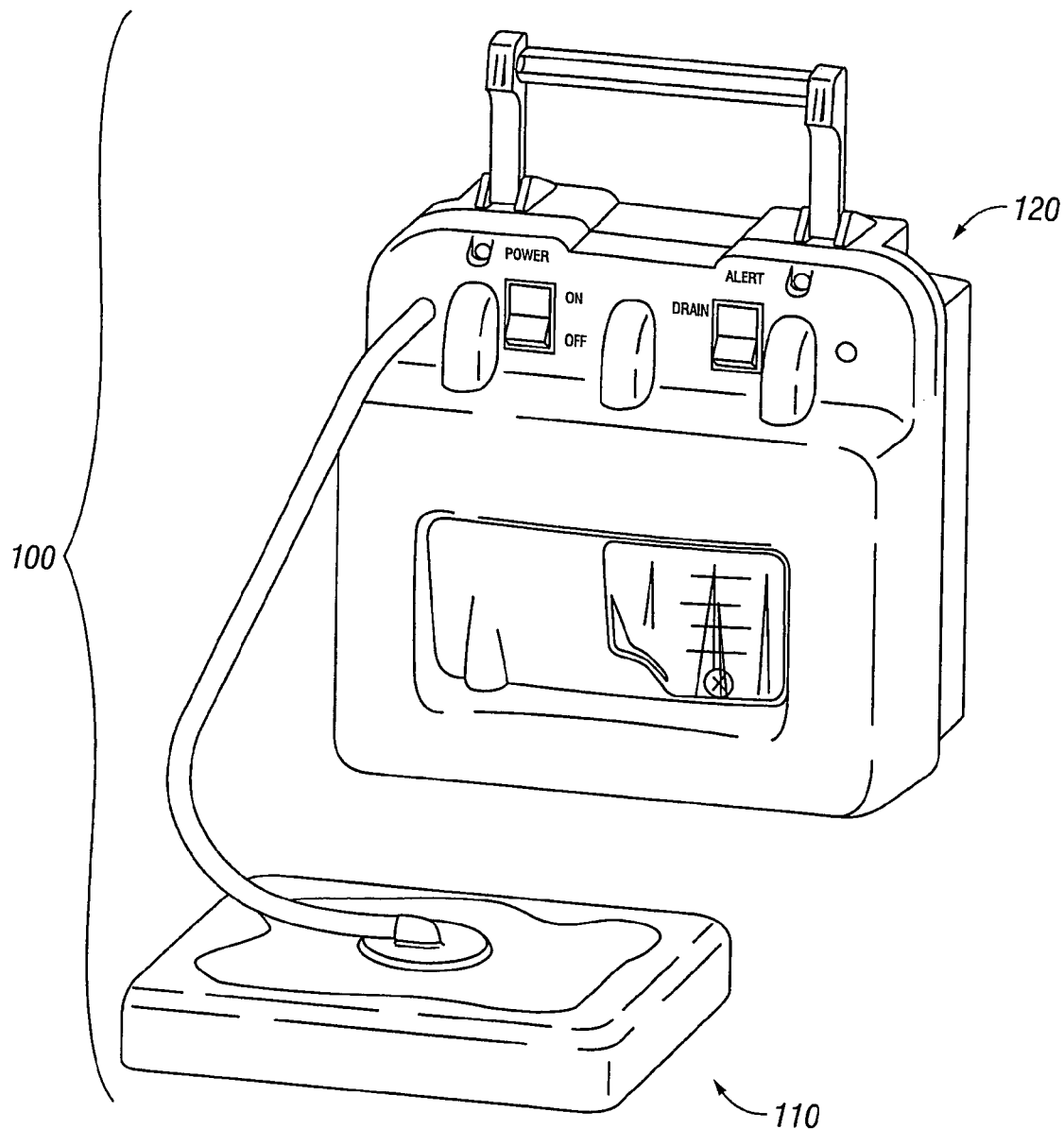
FIG. 1 is a simple illustration of one embodiment of the disclosed compact, self-powered, wound exudate removal and isolation system.

FIG. 1 is a simple illustration of one embodiment of the disclosed compact, self-powered, wound exudate removal and isolation system 100 of the present invention. As shown in FIG. 1, system 100 provides for the collection and disposal of wound exudate through a dressing, which can remain on a wound and be effective well beyond typical dressing change intervals and throughout the entire medical evacuation process. Accordingly, the disclosed system 100 protects the person with a wound, those caring for the person with the wound, and others in close proximity.

The wound exudate removal and isolation system 100 provides a dressing and a cover 110 over the wound, which draws exudate from the wound and moves the exudate to an exudate collection system 120 through the application of a vacuum, or reduced pressure. With traditional reduced pressure delivery systems, the distribution of reduced pressure at the wound site is used to encourage new tissue growth. The wound exudate removal and isolation system 100 is preferably used to isolate, protect, and provide stasis to the wound site until the patient arrives at a medical facility where the wound may be properly treated. The system 100 is therefore configured to provide adequate wound drainage and moisture control capabilities, while minimizing the in-growth of new tissue into the dressing.

Figure 2:
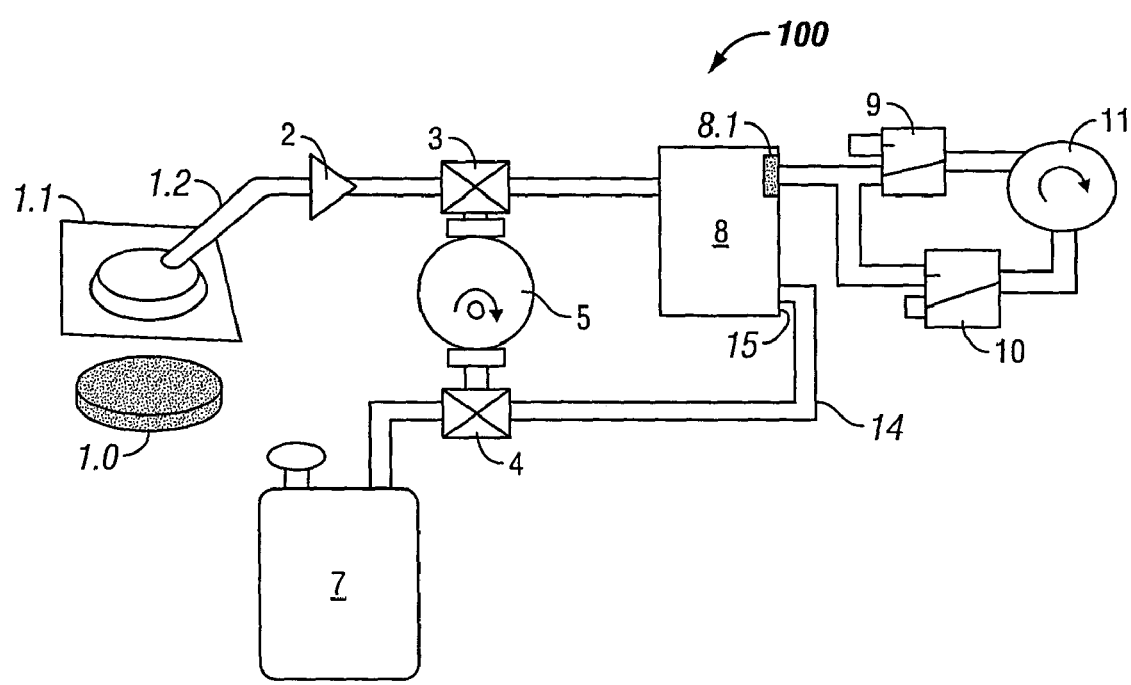
FIG. 2 is a schematic diagram of the wound exudate removal and isolation system according to FIG. 1.

FIG. 2 is a schematic diagram of the wound exudate removal and isolation system 100 according to an embodiment of the present invention. As FIG. 2 illustrates, a porous dressing 1.0 is used to create a protective environment over the wound. Dressing 1.0 is preferably formed from an open-cell, reticulated foam. Alternatively, the dressing may be formed by other materials that are suitable for manifolding pressure across the wound. For example, a solid sheet of material (e.g. a sheet of silicone) having projections on one side may allow the distribution of pressure at the wound through the flow channels formed between the projections. Instead of or in addition to the projections, small holes may be provided in the sheet of material to allow the manifolding of pressure. Whatever type of dressing is used, the dressing 1.0 should have the ability to distribute a reduced pressure to properly draw wound exudate away from the wound. While the system 100 is not designed to encourage granulation tissue growth, studies have found that wounds exposed to reduced pressure may granulate substantially in as little as 48 hours. To assist in the eventual removal and replacement of dressings, the wound contact surface of dressing 1.0 is designed to minimize tissue growth thereby facilitating wound contact well beyond typical 48-72 hour dressing-change intervals.

When a foam dressing is used, the dressing 1.0 dressing includes pores of a size that allow wound exudate to pass from a wound into tubing 1.2., but minimize the in-growth of tissue into the pores. The average pore size is typically between about 40 and 200 µm, and preferably about 100 µm. The pore sizes associated with dressing 1.0 are typically smaller than the pore sizes associated with dressings used to promote wound healing. The porous dressing 1.0 may also have anti-microbial properties. In one embodiment, the dressing may be coated or impregnated with an antimicrobial agent such as silver.

A drape 1.1 is placed over the foam dressing 1.0 to isolate the wound and allow for the application of a reduced pressure to the wound 1.0 through tubing 1.2. In one embodiment, tubing 1.2 is a plastic tubing. The dressing 1.0, the drape 1.1, and a tubing 1.2 may be contained in a small, lightweight kit, which can be easily deployed with and stocked by Forward Military Medical Units.

The reduced pressure applied to the dressing 1.0 is strong enough to continuously draw exudate from the wound through the tubing 1.2. Unlike reduced pressure systems that are used to promote the growth of granulation tissue at the wound, the primary purpose of system 100 is to isolate and contain wounds and remove exudate. While the reduced pressure applied to the wound through the dressing 1.0 may be adjusted depending on the size of the wound and the porosity of the dressing 1.0, it is preferred that the pressure applied to the wound be less than about 125 mmHg. This particular pressure is typically considered the minimum pressure at which new tissue growth is accelerated in wounds; hence, it is desired to remain below this pressure to minimize new tissue growth. More preferably, the pressure applied to the wound through the dressing will be between about 25 and 75 mmHg.

Again referring to FIG. 2 for illustration, a check valve 2 prevents the backflow of exudate into the wound. A push-to-open in-line valve 3 is in fluid communication with check valve 2, positioned downstream from the wound. Downstream from the push-to-open in-line valve 3 is a non-removable, drainable canister 8 in fluid communication with valve 3. In one embodiment, canister 8 is drainable and constructed from a rigid material. A disposal line 14 is fluidly connected to a drainage outlet 15 of the canister 8. A valve 4 is positioned on the disposal line 14 in fluid communication with the canister 8. Both valves 3, 4 are selectively positionable in either an open position or a closed position to allow or prevent fluid flow through the valve 3, 4. Preferably, the placing of valve 3 in an open position results in the valve 4 being placed in a closed position. Similarly, the placing of valve 3 in a closed position results in the valve 4 being placed in an open position. A cam wheel 5 may be operably connected to both valves 3, 4 to mechanically coordinate the simultaneous positioning of the valves 3, 4.

Since the system 100 may be placed at the wound for extended periods of time during patient transport, it may be desired to drain the canister 8 while leaving the remainder of the system 100 in place. Valves 3, 4 are provided to allow drainage of the canister 8 when full or when desired by the person attending to the wound. During the application of reduced pressure to the wound, valve 3 is open to provide fluid communication between the dressing 1.0 and the canister 8. In this configuration, valve 4 is closed to prevent drainage of the canister 8. To drain the canister 8, valve 3 is closed and valve 4 is opened. The closing of valve 3 prevents reduced pressure from being applied to the wound, while the opening of valve 4 allows wound exudate in the canister 8 to drain through the disposal line 14. Optionally, a disposable container 7 may be connected to the disposal line 14 to collect the wound exudate drained from the canister 8. The disposable container 7 may be a flexible, vented disposal bag. When the disposable container 7 is full, it may be removed and replaced with an empty container.

Reduced pressure is provided to the dressing 1.0 through the canister by a pump 11 that is fluidly connected to the canister. In one embodiment pump 11 is a battery-operated vacuum/pressure pump. Alternatively, the pump 11 may be manually operated, or may be any other pump suitable for inducing the pressures disclosed herein. As the pump 11 applies a reduced pressure to the dressing 1.0 through the canister 8, wound exudate is drawn from the wound and deposited in canister 8. This operation occurs when the valve 3 is in an open position and the valve 4 is in a closed position.

As previously described, the canister 8 may be drained by positioning valve 3 in a closed position and valve 4 in an open position. While the drainage operation may be facilitated by gravitational force, the wound exudate may alternatively be forced out of the canister 8 into the disposal line 14 by the pump 11. To facilitate forced drainage of the canister 8, a three-way valve 9 is fluidly connected between the canister 8 and an inlet of the pump 11. The valve 9 is selectively positionable between an active position and a vent position. In the active position, the valve 9 allows fluid communication between the canister and the inlet of the pump 11. In the vent position, the inlet of the pump 11 is vented. Another three-way valve 10 is fluidly connected between the canister 8 and an outlet of the pump 11. The valve 10 is selectively positionable between an active position and a vent position. In the active position, the valve 10 allows fluid communication between the canister and the outlet of the pump 11. In the vent position, the outlet of the pump 11 is vented. The positioning of the valves 9, 10 is linked such that a positioning of the valve 9 in the active position results in a positioning of the valve 10 in the vent position. Similarly, a positioning of the valve 9 in the vent position results in a positioning of the valve 10 in the active position.

When valve 9 is positioned in the active position and valve 10 is positioned in the vent position, the pump 11 is configured to draw wound exudate from the dressing 1.0 into the canister 8. In this reduced pressure configuration, valve 3 is positioned in the open position and valve 4 is positioned in the closed position. When valve 9 is positioned in the vent position and valve 10 is positioned in the active position, the pump 11 is configured to provide a positive pressure to the canister to force wound exudate from the canister 8 into the disposal line 14. In this positive pressure configuration, valve 3 is positioned in the closed position and valve 4 is positioned in the open position.

A hydrophobic filter 8.1 also may be included in fluid communication with the canister 8 to prevent fluid from entering the tubing attached to pump 11 and valves 9 and 10.

In one embodiment, a sensor may be operably associated with the canister 8 to detect when the canister 8 is full of wound exudate. The sensor may be operably connected to the valves 3, 4, 9, 10 to automatically adjust the operation of the system 100 from a reduced pressure system to a positive pressure system so that exudate is moved from the canister 8 to the disposable container 7 when the canister 8 is full.

The system may further include a safety alarm system that provides either an audio signal or a visual signal if the system is not operating properly. The safety alarm system is configured to avoid producing false alarms in response to typical patient conditions that may occur during the medical evacuation process. However, some events that may be detected by the safety alarm system include, but are not limited to, leak detection events, blockage events, full canister events, low pressure events, high pressure events, and low battery events.

The system may also include blood detection sensors to prevent exsanguination or the removal of copious or unhealthy amounts of blood from a patient.

Figure 3:
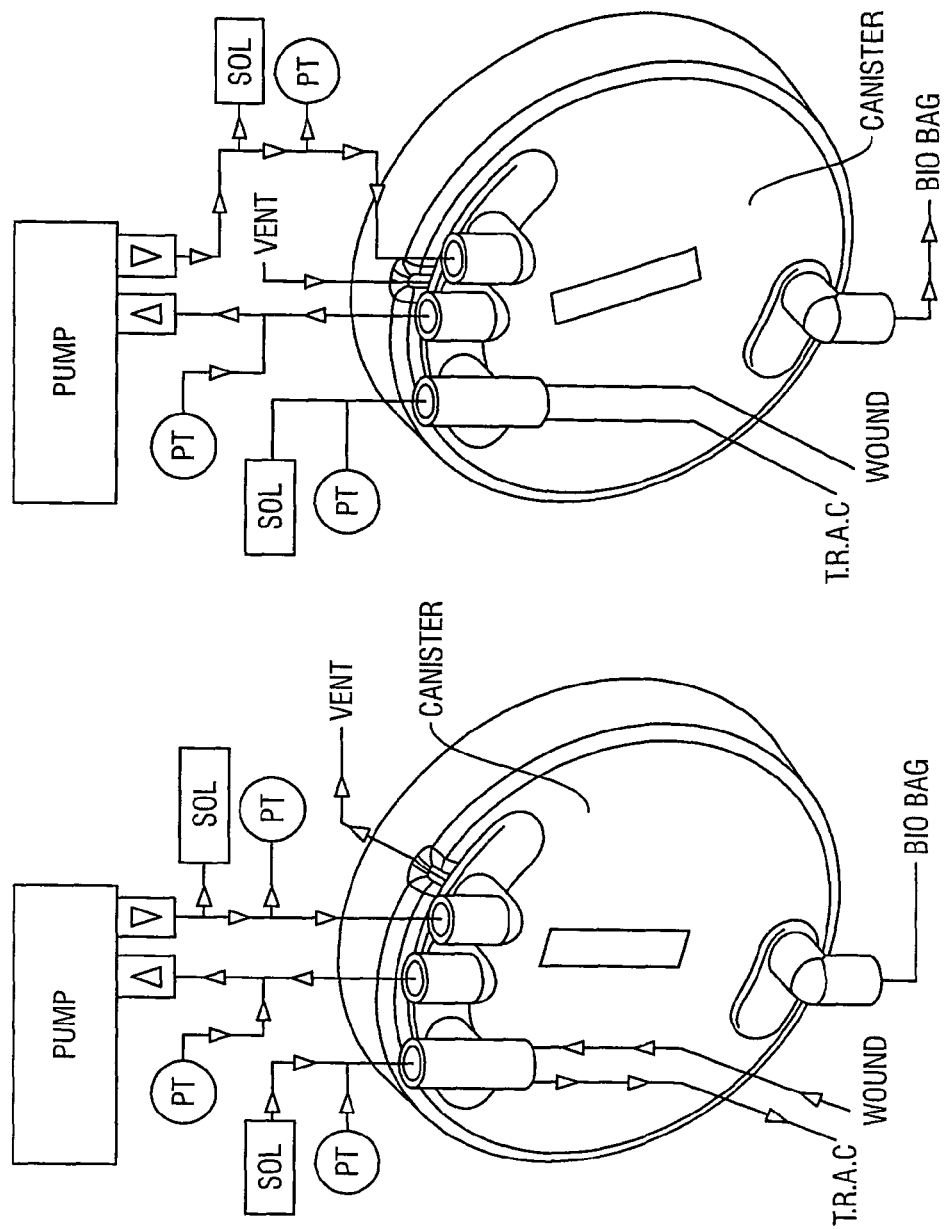
FIG. 3 is a schematic diagram of an alternative embodiment of the wound exudate removal and isolation system in which a valve is activated by rotating the canister.

As shown in FIG. 3, the valve directing the flow of exudate may be manually activated by rotation of the canister 8.

It should be apparent from the foregoing that an invention having significant advantages has been provided. While the invention is shown in only a few of its forms, it is not just limited but is susceptible to various changes and modifications without departing from the spirit thereof.

We claim:

1. A wound treatment apparatus comprising:
   a porous dressing;
   a canister in fluid communication with the porous dressing;
   a first valve positioned between the porous dressing and the canister and positionable in an open position to allow fluid flow and a closed position to prevent fluid flow between the porous dressing and the canister;
   a disposal line fluidly connected to the canister;
   a second valve operably positioned within the disposal line and positionable in an open position to allow fluid flow and a closed position to prevent fluid flow through the disposal line; and
   a pump in fluid communication with the canister and operable to draw wound exudate from the porous dressing into the canister when the first valve is open and the second valve is closed, the pump further being operable to force wound exudate from the canister into the disposal line when the first valve is closed and the second valve is open;
   wherein the operation of the first and second valves is coordinated such that when the first valve is opened, the second valve is closed, and when the first valve is closed, the second valve is opened.

2. The apparatus of claim 1, wherein the porous dressing is an open-cell, reticulated foam.

3. The apparatus of claim 1, wherein an average pore size of the porous dressing is less than about 200 microns.

4. The apparatus of claim 1, wherein an average pore size of the porous dressing is less than or equal to about 100 microns.

5. The apparatus of claim 1, wherein the porous dressing is comprised of a material that minimizes tissue growth into the porous dressing.

6. The apparatus of claim 1, wherein the porous dressing includes an antimicrobial agent.

7. The apparatus of claim 1, further comprising:
   a third valve positioned between the canister and an inlet of the pump, the third valve being positionable in an active position in which the canister is in fluid communication with the inlet of the pump and a vent position in which the inlet of the pump is vented; and
   a fourth valve positioned between the canister and an outlet of the pump, the fourth valve being positionable in an active position in which the canister is in fluid communication with the outlet of the pump and a vent position in which the outlet of the pump is vented.

8. The apparatus of claim 7, wherein:
the pump is configured to draw wound exudate from the porous dressing into the canister when the third valve is in the active position and the fourth valve is in the vent position; and
the pump is configured to force wound exudate from the canister into the disposal line when the third valve is in the vent position and the fourth valve is in the active position.

9. The apparatus of claim 1, further comprising a disposable container connectable to the disposal line to collect wound exudate from the canister when the first valve is closed and the second valve is open.

10. The apparatus of claim 1, further comprising a sensor operably connected to the canister and the first and second valves to close the first valve and open the second valve when the wound exudate in the canister reaches a predetermined level.

11. The apparatus of claim 1; further comprising a check valve positioned between the porous dressing and the canister to prevent backflow of wound exudate from the canister to the porous dressing.

12. The apparatus of claim 1, further comprising a safety alarm to alert an operator if an event is detected that includes at least one of a leak detection event, a blockage event, a full canister event, a low pressure event, a high pressure event, and a low battery event.

13. The apparatus of claim 1, further comprising a blood detection sensor.

14. A wound treatment apparatus comprising:
a porous dressing;
a canister in fluid communication with the porous dressing;
a first valve positioned between the porous dressing and the canister and positionable in an open position to allow fluid flow and a closed position to prevent fluid flow between the porous dressing and the canister;
a disposal line fluidly connected to the canister;
a second valve operably positioned within the disposal line and positionable in an open position to allow fluid flow and a closed position to prevent fluid flow through the disposal line;
a pump in fluid communication with the canister and operable to draw wound exudate from the porous dressing into the canister when the first valve is open and the second valve is closed, the pump further being operable to force wound exudate from the canister into the disposal line when the first valve is closed and the second valve is open;

a third valve positioned between the canister and an inlet of the pump, the third valve being positionable in an active position in which the canister is in fluid communication with the inlet of the pump and a vent position in which the inlet of the pump is vented;
a fourth valve positioned between the canister and an outlet of the pump, the fourth valve being positionable in an active position in which the canister is in fluid communication with the outlet of the pump and a vent position in which the outlet of the pump is vented; and
a check valve positioned between the porous dressing and the canister to prevent backflow of wound exudate from the canister to the porous dressing;
wherein the operation of the first and second valves is coordinated such that when the first valve is opened, the second valve is closed, and when the first valve is closed, the second valve is opened.

15. The apparatus of claim 14, wherein:
the pump is configured to draw wound exudate from the porous dressing into the canister when the third valve is in the active position and the fourth valve is in the vent position; and
the pump is configured to force wound exudate from the canister into the disposal line when the third valve is in the vent position and the fourth valve is in the active position.

16. The apparatus of claim 14, further comprising a disposable container connectable to the disposal line to collect wound exudate from the canister when the first valve is closed and the second valve is open.

17. The apparatus of claim 14, further comprising a sensor operably connected to the canister and the first and second valves to close the first valve and open the second valve when the wound exudate in the canister reaches a predetermined level.

18. The apparatus of claim 14, further comprising a safety alarm to alert an operator if an event is detected that includes at least one of a leak detection event, a blockage event, a full canister event, a low pressure event, a high pressure event, and a low battery event.

19. The apparatus of claim 14, further comprising:
a cam wheel coupled to the first valve and the second valve, the cam wheel mechanically coordinating the simultaneous positioning of the first valve and the second valve.

20. The apparatus of claim 1, further comprising:
a cam wheel coupled to the first valve and the second valve, the cam wheel mechanically coordinating the simultaneous positioning of the first valve and the second valve.

* * * * *